United States Patent [19]

Ollivier

[11] 4,452,678

[45] Jun. 5, 1984

[54] PROCESS AND APPARATUS FOR THE PHOTOCHEMICAL PRODUCTION OF HALOGENO-ALKANES AND CYCLOALKANES

[75] Inventor: Jean Ollivier, Croix de Buzy, France

[73] Assignee: Societe Nationale Elf Aquitaine, France

[21] Appl. No.: 481,855

[22] Filed: Apr. 4, 1983

[30] Foreign Application Priority Data

Apr. 7, 1982 [FR] France ................................. 82 06031

[51] Int. Cl.³ ........................ C07C 17/00; C07G 13/00
[52] U.S. Cl. ......................... 204/163 R; 204/158 HA; 422/186.3
[58] Field of Search .................... 204/163 R, 158 HA; 422/186.3

[56] References Cited

U.S. PATENT DOCUMENTS

| | | | |
|---|---|---|---|
| 2,683,688 | 7/1954 | Tramm et al. | 204/163 R |
| 3,402,114 | 9/1968 | Hutson et al. | 204/158 HA |
| 3,494,844 | 2/1970 | Holiday | 204/163 R |
| 3,745,103 | 7/1973 | Richtzenhain | 204/163 R |
| 3,845,317 | 10/1974 | Lindwall | 422/186.3 |

*Primary Examiner*—John F. Niebling
*Attorney, Agent, or Firm*—Ostrolenk, Faber, Gerb & Soffen

[57] ABSTRACT

Halogenation of alkanes and of cycloalkanes by the action of ultraviolet upon a solution of the halogen in the alkane; the solution is prepared in advance and passes into the irradiated zone, after having been put into contact with a halogenation inhibitor. Preferably, the inhibitor, which is a metal of Group VB of the Periodic Classification, is also provided at the outlet from the reactor.

19 Claims, 2 Drawing Figures

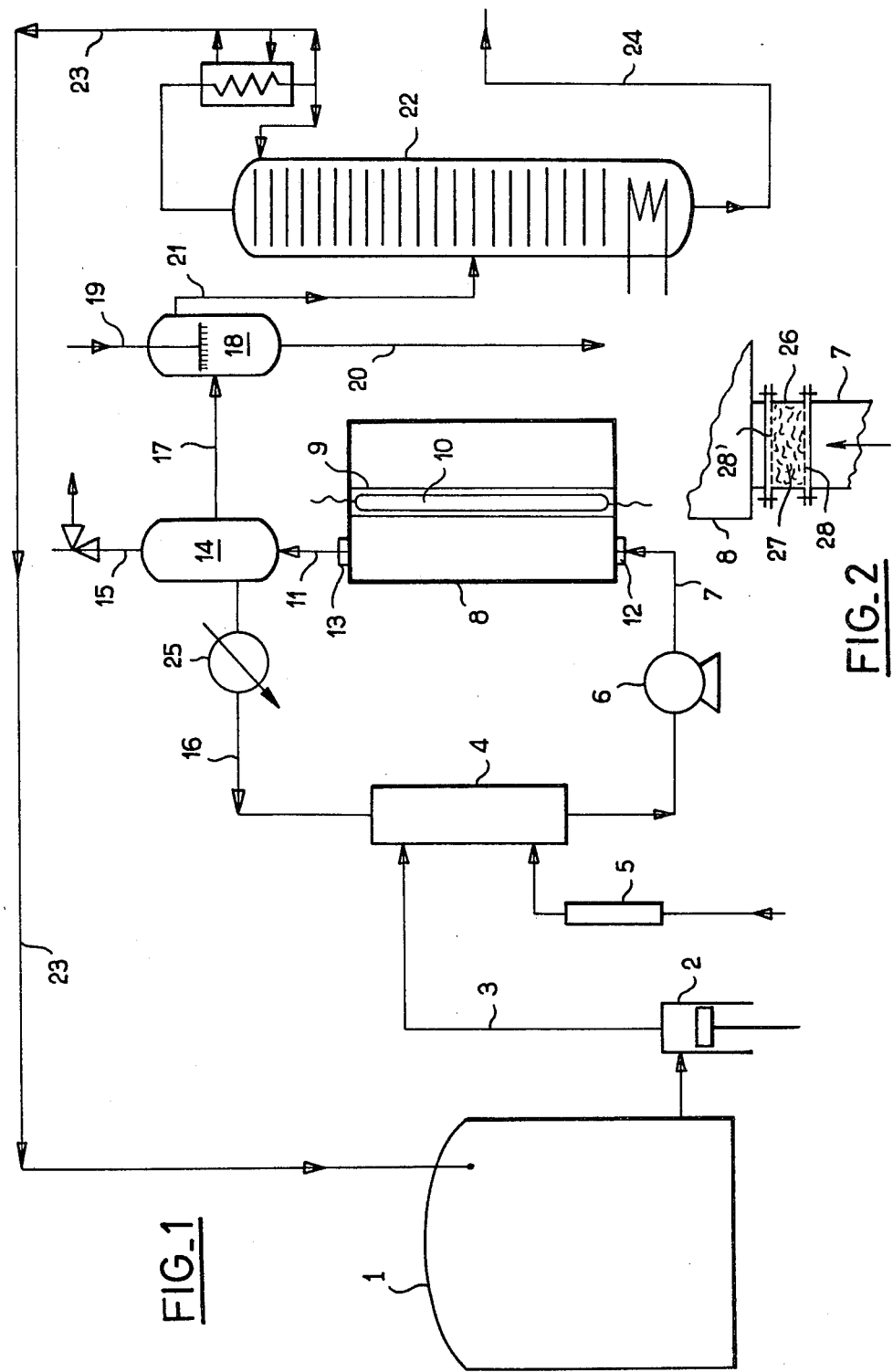

of resistant material, in order to retain the inhibitor in place, preventing its entrainment by the liquid flow of the reactants treated.

This preferred embodiment is illustrated diagrammatically in FIG. 2, the description of which is given below following that of an installation, FIG. 1, comprising a cladding of inhibitor metal according to the invention.

As indicated above, the surface offered by the inhibitor metal is of the order of 100 to 10,000 $cm^2/cm^2$ of the section of the inlet and the outlet of the photochemical reactor. It is to be noted however that the surface necessarily depends equally on the speed of the liquid treated. In fact, the higher this speed at the reactor inlet, the lesser are the risks of the propagation of free radicals upstream of the reactor; conversely, the higher the speed, the greater are the risks of entrainment of such radicals, propagating the reaction, at the outlet of the photochemical reactor. Consequently, at low liquid speeds, the inhibitor surfaces should correspond to the upper limits indicated at the reactor inlet; in contrast, the lower surface limits suffice at the outlet, when the speed is low. The converse is true for high speeds of flow of the liquid.

In practice, the values of the surface indicated above are suitable for speeds of about 0.05 to 5 m/sec at the reactor inlet.

The application of an inhibitor at the inlet to the photochemical reactor according to the invention has considerable importance; in contrast, it is possible to utilise low inhibitor surfaces or even to suppress them completely at the outlet, in the embodiment of the invention which consists of regulating the proportion of halogen in such a manner that it is entirely combined during passage of the reaction liquid through the region subjected to ultraviolet. In these conditions, as there is no halogen at the reactor outlet, the reaction cannot continue beyond there. As it is possible to have free radicals created accidentally in the recycling circuit, which initiate the reaction in the recycled liquid at the chlorine injection point, the precaution according to the invention nevertheless remains valid and useful; in other words, it is always of interest to utilize a cladding of the inhibitor at the reactor outlet.

As regards the general conditions of synthesis according to the invention, they are similar to those of the prior art; thus the temperature can advantageously range from 0° to 50° and preferably from 10° to 30° C.; UV can be employed having wavelengths of 250 to 400 nm and more particularly of 350 nm, the residence time of the reaction mixture in the photochemical reactor being of the order of 1 to 300 sec and more particularly of 3 to 150 sec.

As in the known art, the process according to the invention is preferably carried out with a large excess of the alkane or cycloalkane with respect to the halogen. Thus, in the preparation of cyclohexyl chloride, it is advantageous to have at least 5 moles of cyclohexane per mole of chlorine, this proportion possibly ranging from 200 to 1.

The invention illustrated by the Examples given further below can be carried out in an apparatus represented in the accompanying drawings.

FIG. 1 is a general diagram of an installation for the chlorination of a liquid alkane or cycloalkane.

FIG. 2 shows a diagrammatic axial cross-section of the region at the base of the photochemical reactor with a portion of the inlet duct for the reactants at this base.

In the drawing, 1 designates a storage reservoir for cyclohexane, 2 a pump connected to the base of this reservoir, 3 a duct for transferring cyclohexane into the mixer 4. The chlorine, which is fed from a reservoir (not shown) to the pump 5, is introduced into the lower part of the mixer 4; the solution of chlorine in the cyclohexane is withdrawn from the mixer 4 by the pump 6 in order to be injected via the duct 7 into the base of the reactor 8. The latter contains an axial tube 9 of quartz, in which is located an ultraviolet lamp 10; a pipe 11 constitutes the outlet at the top of the reactor 8.

In accordance with the original characteristic of the invention, at the inlet to the reactor 8, the duct 7 ends at a housing 12 containing tantalum turnings. A similar housing 13 is located at the junction of the outlet pipe 11 with the reactor 8; this housing 13 also contains turnings of tantalum.

The pipe 11 connects the reactor to the base of a separator 14 where the gases are evacuated via an upper pipe 15. From the lower part of the separator 14, a recycling duct 16 is connected which supplies the major part of the reaction medium to the top of the mixer 4; a heat exchanger 25 is connected to the duct 16, allowing cooling of the recycled liquid to the desired temperature. At a higher level than that of the duct 16, an outlet 17 is located, through which the remaining cyclohexane, the cyclohexyl chloride formed and the HCl pass to a scrubber 18, in which water introduced via 19 eliminates the hydrochloric acid in the form of an aqueous solution, removed at the bottom via 20. The cyclohexane-cyclohexyl chloride mixture thus scrubbed passes through the duct 21 into a distillation column 22; the cyclohexane distilled at the top of the column returns via 23 to the storage reservoir 1, while the crude cyclohexyl chloride passes from the base of the column 22 via the duct 24 to a standard rectification column, not shown.

In FIG. 2, the base of the photochemical reactor 8 is shown, to which the duct 7 is connected by means of a housing 26. At the inlet to the latter, a grid or sheet 28 of material inert to hydrochloric acid is inserted; at the outlet of the housing 26, a second similar perforated grid or sheet 28' is located. The interior of the housing is filled with turnings or filaments 27 of a metal inhibiting the reaction. The grids 28 and 28' are calculated so as to allow free passage of the liquid from the duct 7 without permitting entrainment of the turnings or filaments 27.

EXAMPLES 1 TO 6

In a glass apparatus of laboratory scale according to the diagram of FIG. 1, a series of tests for the chlorination of cyclohexane have been effected, with or without the provision of tantalum turnings at the inlet to the reactor. The volume of the reactor was 160 ml, the supply of chlorine was 11 to 12 l/hr measured at 0°/760 mm Hg.

The temperature in the reactor was maintained at 22° to 23° C. The residence time in the reactor was regulated so that all the chlorine was consumed before the outlet of the reactor, while the rate of circulation in the recycling circuit 16-4-6 was modified from one test to another. The maximum duration of passage through the recycling circuit was 0 hrs 32, the supply of fresh cyclohexane being 500 ml/h. The inlet to the reactor comprised a tube of 5 mm interior diameter in which was placed over a height of 2 cm a plug of 2 g of tantalum in the form of turnings having a thickness of 0.2 mm;

PROCESS AND APPARATUS FOR THE PHOTOCHEMICAL PRODUCTION OF HALOGENO-ALKANES AND CYCLOALKANES

The invention relates to the manufacture of halogeno-alkanes and halogeno-cycloalkanes in the liquid phase, by the action of chlorine on the corresponding hydrocarbon. It provides an improved process, as well as an apparatus for carrying out this process. The invention can apply very advantageously to the production of chloro-cycloalkanes, in particular cyclohexyl monochloride.

In view of the importance of halogeno-alkanes and cycloalkanes, particularly cyclohexyl chloride, as intermediates in the production of various useful compounds, the preparation of these compounds has given rise to a number of industrial methods. Among current procedures, the most practical consists of passing a solution of chlorine in cyclohexane into a reactor in which an ultraviolet light emitter is located; the monochlorocyclohexane so formed is then separated by distillation from the remaining cyclohexane. However, in the industrial practice of this method, the disadvantage of an overvigorous chlorination arises, leading to polychlorinated derivatives of cyclohexane, reducing the selectivity of the reaction for the desired monochlorocyclohexane. Quantities of the order of more than 10% of the cyclohexane are thus lost in the form of polychlorinated compounds, as can be seen for example from the Table on page 2 of French Pat. No. 1254403 or from Table 1 of U.S. Pat. No. 3,494,844. This disadvantage is attributed by certain workers to the reaction of chlorine with cyclohexane in the dark before the reaction mixture arrives in the zone where the emission of ultraviolet takes place. In these circumstances, a process has been devised which consists of introducing a small proportion of oxygen into the reaction medium in order to inhibit chlorination in the dark; this means should ensure that the reaction only commences when the mixture is irradiated by ultraviolet. However, the introduction of oxygen into the reaction medium involves risks against which it is necessary to take certain quite strict precautions, both because of the dangers presented by the introduction of oxygen into the hydrocarbon and because of the inhibitive action of the oxygen on the photochemical reaction itself. It is thus necessary rigorously to control the input of oxygen into the supply circuit, so that its content is only of the order of 5 to 10 ppm, taking into account the oxygen normally present in the reactants. On the other hand, the luminous power to be supplied to the reactor must be increased because of the above-mentioned inhibitive action. It is to be noted that peroxides formed from the oxygen present lead to the formation of impurities, particularly cyclohexanol.

The present invention allows the above-mentioned disadvantages to be avoided and leads to very high selectivities of more than 96% for monochlorocyclohexane with respect to the cyclohexane converted. It renders possible very regular conduct of the preparation, without risk and without the formation of material quantities of by-products.

The invention is based upon the quite surprising discovery made by the Applicants concerning the propagation of the halogenation reaction in the dark, which precedes the irradiation with ultraviolet; the astonishing conclusion has been reached that this reaction in the dark areas upstream of the reactor is due to the propagation of the reaction initiated in the photochemical reactor. In effect, it has been found that, by disposing a chlorination inhibitor in the reactor inlet, chlorination no longer occurs in the apparatus and ducts upstream of the reactor, where dissolution of the chlorine in the cyclohexane takes place.

The process according to the invention is thus characterized in that a solid substance insoluble in the reaction medium and inhibiting halogenation is located in the inlet region of the photochemical reactor.

More particularly, the process according to the invention consists in placing, inside an inlet region of the reactor, a metal capable of inhibiting chlorination of the hydrocarbon. According to a preferred feature of the invention, the inhibitor metal is selected from Group VB of the Periodic Classification of the Elements, that is it is constituted by one or more of the metals vanadium, niobium and tantalum. Tantalum is particularly useful because of its high reactivity vis-à-vis radicals and atoms and its chemical inertia vis-à-vis the reaction medium which is rich in hydrochloric acid.

Preferably, such an inhibitor is also located in the outlet region of the reactor, which avoids continuance of the reaction outside the reactor in the case where the effluent contains chlorine.

While the inhibition according to the invention is a phenomenon of the catalytic type requiring only a small quantity of the inhibitor metal, it is preferable for the contact surface of the inhibitor with the liquid entering the reactor to be sufficient for inhibition to occur at all points in the stream of liquid flowing towards the reactor. It is thus recommendable for the surface offered by the metal in the inlet and outlet regions of the photochemical reactor to be of the order of 100 to 10,000 $cm^2/cm^2$ of cross-section of the liquid flow traversing these regions. In any case, the weight and volume of the metal inhibitor employed are incomparably lower than those of the materials of construction of the reactor and the ducts concerned.

The inhibitive effect on propagation of free radicals by the employment of the present invention can be obtained in various ways. In particular, it is possible to cover the interior walls of the inlet and outlet ducts of the photochemical reactor over a certain length with a cladding of the inhibitor metal. However, to ensure better contact between the reaction liquid and the metal, it is preferable to provide it, in a form having a large surface, transversely of the liquid stream. Thus, the metal can be placed in the form of one or more perforated plates or grids perpendicular to the flow of liquid in the conduits in question. A structure like a static mixer is particularly recommendable. As the inhibitor metals are quite costly, these very thin plates or grids are supported on thicker perforated or grid-like sheets of a resistant material, particularly a ceramic, glass or metal inert to the reaction medium.

As it is useful to utilize the inhibitor, in particular vanadium, niobium or tantalum, in a form having a surface as large as possible for a minimum of weight, the means preferred consist in providing these metals as fine filaments or turnings of small thickness. Thus, it is recommendable to provide filaments having a cross-section of about 0.05 to 1 mm and preferably 0.1 to 0.5 mm in diameter or turnings having a thickness of the same order of size. In this case, it is convenient to locate the filaments and/or turnings in a housing or recess defined on one side and the other by grids or perforated sheets this plug was removed for the tests of Examples 5 and 6. Table I gives the results of these tests.

Comparison of the production results and selectivities of Examples 5 to 6 with those of Examples 1 to 4 shows the marked advantage of the employment of an inhibitor at the reactor inlet; it can be seen that, with the latter, selectivities of 94.5 are attained, in contrast to a maximum of 86.2 in the absence of the inhibitor.

These Examples show also that it is possible to operate with much higher speeds at the reactor inlet, leading to residence times in the latter which are much lower.

EXAMPLES 7 TO 11

In the apparatus of the foregoing Examples, where the photochemical reactor with a coaxial UV lamp emitting at a peak of 350 nm has a capacity of 160 ml, cyclohexyl chloride was produced continuously; cyclohexane was supplied in excess with respect to the $Cl_2$ such that its rate of conversion to the monochlorinated derivative remained low, in the limits of 11% to 18%, the chlorine being completely consumed in the reactor. The supplies of reactants in absolute values were varied, as well as the output of the ultraviolet lamp. In Examples 7 to 9, the tantalum cladding was the same as in Examples 1 to 4, while Examples 10 and 11 were carried out without any inhibitor.

The results are summarised in Table II. It can be seen that with the tantalum cladding selectivities of the product desired are 92% to 94%, against 81% to 84% in the absence of such an inhibitor; also, in Examples 10 and 11, the chlorine is consumed in the inlet duct for the reaction mixture, while it is not consumed in Examples 7 to 9.

TABLE I

| | with inhibitor | | | | without inhibitor | |
|---|---|---|---|---|---|---|
| Example No | 1 | 2 | 3 | 4 | 5 | 6 |
| Recycling rate l/h | 5 | 35 | 70 | 150 | 5 | 150 |
| Linear speed at the reactor inlet m/sec | 0.07 | 0.5 | 1 | 2.13 | 0.07 | 2.13 |
| Moles/liter $Cl_2$ at the reactor inlet | 0.1 | 0.0143 | 0.00414 | 0.00373 | 0.1 | 0.00373 |
| Residence time in the reactor, sec. | 115.2 | 16.46 | 8.23 | 3.84 | 115.2 | 3.84 |
| Percentage conversion of cyclohexane | 11.24 | 11.35 | 13.80 | 11.43 | 11.24 | 11.43 |
| Production of monochlorocyclohexane g/h. | 71.5 | 56.54 | 71.8 | 65.3 | 56.0 | 57.2 |
| Selectivity in monochloro-cyclohexane mole % | 94.5 | 93.5 | 93.6 | 94.2 | 86.2 | 82.5 |

TABLE II

| | Operative conditions | | | | |
|---|---|---|---|---|---|
| | with inhibitor | | | without inhibitor | |
| Example No. | 7 | 8 | 9 | 10 | 11 |
| Cyclohexane supply ml/h | 543 | 580 | 5000 | 543 | 5000 |
| $Cl_2$ gas supply l/h | 11.5 | 21 | 130 | 11.5 | 130 |
| Molar ratio cyclohexane/$Cl_2$ | 9.66 | 5.77 | 7.84 | 9.66 | 7.84 |
| Electric power of the lamp in watts | 3.2 | 0.6 | 3.2 | 3.2 | 3.2 |
| % conversion of cyclohexane | 11.4 | 18.5 | 13.2 | 11.6 | 13.3 |
| Production of monochlorocyclohexane g/l/h | 408 | 648 | 4493 | 361 | 3910 |
| Selectivity in mono-chlorocyclohexane % | 94.2 | 92 | 94 | 83.4 | 81.8 |

I claim:

1. In a process of halogenating an alkane or cycloalkane by passing a solution of halogen in the alkane or cycloalkane through a zone irradiated by ultraviolet light, the improvement which comprises disposing at least one metal of Group VB of the Periodic Classification of Elements at the inlet of said zone, whereby the solution comes into contact with the metal when flowing to the zone of irradiation.

2. The process according to claim 1 wherein the metal has a surface area of 100 to 10,000 $cm^2/cm^2$ of the cross section of the liquid vein formed by the solution when flowing into the irradiation zone.

3. The process according to claim 1 wherein the metal is also disposed at the outlet of the zone of irradiation.

4. The process according to claim 3 wherein the metal has a surface area of 100 to 10,000 $cm^2/cm^2$ of the liquid vein formed by the solution when leaving the zone of irradiation.

5. The process according to claim 1 wherein the metal is tantalum.

6. The process according to claim 1 wherein the metal is vanadium.

7. The process according to claim 1 wherein the metal is niobium.

8. In a process of monochlorinating cyclohexane by passing a solution of chlorine in cyclohexane through a zone irradiated by ultraviolet light, the improvement which comprises disposing pieces of at least one metal of Group VB of the Periodic Classification of Elements at the inlet of the zone of irradiation such that the solution comes into contact with the pieces when flowing to the zone of irradiation.

9. The process according to claim 8 wherein the surface area of the pieces of metal is 100 to 10,000 $cm^2/cm^2$ of cross section of the liquid vein formed by the solution flowing into the zone of irradiation.

10. The process according to claim 9 wherein pieces of the metal are also disposed at the outlet of the zone of irradiation.

11. The process of claim 10 wherein the metal is tantalum.

12. The process of claim 8 wherein the pieces of metal are turnings or filaments of tantalum.

13. The process of claim 8 wherein the pieces of metal are turnings or filaments of vanadium.

14. The process of claim 8 wherein the pieces of metal are turnings or filaments of niobium.

15. In an apparatus for halogenating an alkane or cycloalkane by passing a solution of halogen in the alkane or cycloalkane through a zone irradiated by ultraviolet light comprising a reactor containing an ultraviolet light, a mixer for receiving the alkane or cycloalkane and the halogen, means to transport material in the mixer to the reactor, a separator, and means to transport material from the reactor to the separator, the improvement which comprises at least one metal of Group VB of the Periodic Classification of Elements disposed at the inlet of the reactor.

16. The apparatus of claim 15 wherein at least one metal of Group VB of the periodic classification of elements is disposed at the outlet of the reactor.

17. The apparatus according to claim 16 wherein the metal is pieces of tantalum.

18. The apparatus according to claim 15 wherein the metal is turnings or filaments of tantalum.

19. The apparatus according to claim 15 wherein the metal or turnings or filaments of vanadium or niobium.

* * * * *